US009645096B2

(12) United States Patent
Cai et al.

(10) Patent No.: US 9,645,096 B2
(45) Date of Patent: May 9, 2017

(54) METHOD AND SYSTEM FOR OPTICAL MEASUREMENTS (71) Applicant: Semiconductor Manufacturing International (Shanghai) Corporation, Shanghai (CN)

(72) Inventors: Boxiu Cai, Shanghai (CN); Yi Huang, Shanghai (CN)

(73) Assignee: SEMICONDUCTOR MANUFACTURING INTERNATIONAL (SHANGHAI) CORPORATION, Shanghai (CN)

( * ) Notice: Subject to any disclaimer, the term of this patent is extended or adjusted under 35 U.S.C. 154(b) by 0 days.

(21) Appl. No.: 14/861,273

(22) Filed: Sep. 22, 2015

(65) Prior Publication Data

US 2016/0091436 A1 Mar. 31, 2016

(30) Foreign Application Priority Data

Sep. 26, 2014 (CN) .......................... 2014 1 0505496

(51) Int. Cl.
*G01N 21/00* (2006.01)
*G01N 21/95* (2006.01)
*G01N 21/956* (2006.01)

(52) U.S. Cl.
CPC ... *G01N 21/9501* (2013.01); *G01N 21/95607* (2013.01)

(58) Field of Classification Search
CPC .......... G01N 21/9501; G01N 21/4738; G01N 21/95607
USPC ..... 356/337–343, 237.1–237.6, 239.1–239.8
See application file for complete search history.

(56) References Cited

U.S. PATENT DOCUMENTS

2012/0038915 A1* 2/2012 Tsuchida .................. G01J 3/02
356/301

* cited by examiner

*Primary Examiner* — Tri T Ton
(74) *Attorney, Agent, or Firm* — Anova Law Group, PLLC (57) ABSTRACT

The present disclosure includes a method for optical measurements. The method includes providing a substrate with a structure for optical measurement on the substrate; and illuminating a light spot on the structure for optical measurement to obtain a measured light scattering spectrum. The method also includes performing a first matching process to obtain a plurality of matching standard optical scattering spectra and a plurality of first matching degrees, each standard optical scattering spectrum corresponding to one first matching degree; obtaining a plurality of combined optical scattering spectra based on the plurality of matching standard optical scattering spectra; and performing a second matching process to obtain a plurality second matching degree, each corresponding to one combined optical scattering spectrum.

18 Claims, 5 Drawing Sheets

METHOD AND SYSTEM FOR OPTICAL MEASUREMENTS

CROSS-REFERENCES TO RELATED APPLICATIONS

This application claims the priority of Chinese Patent Application No. 201410505496.8 filed on Sep. 26, 2014, the entire content of which is incorporated herein by reference.

FIELD OF THE DISCLOSURE

The present disclosure relates to the field of semiconductor technology, more particularly, relates to a method and a system for optical measurements.

BACKGROUND

Figure 1:
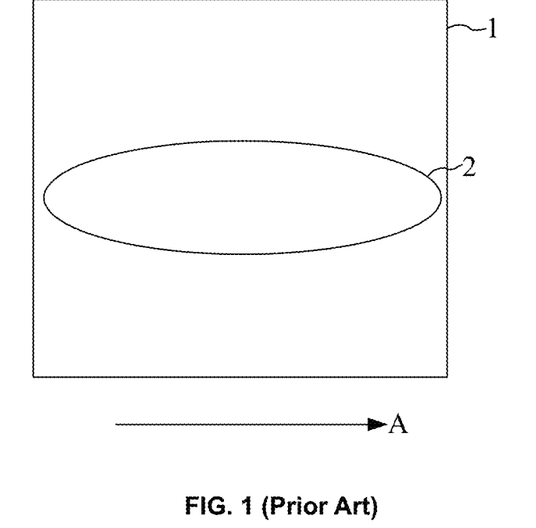
FIG. 1 illustrates the conventional measurement technique without light spot deviation.

In conventional semiconductor technology, optical measurement techniques may be used to monitor and test structural parameters of semiconductor devices in semiconductor manufacturing, such as a feature size of a semiconductor device. Specifically, in semiconductor manufacturing, when a semiconductor device is being formed on a substrate, a corresponding structure for optical measurement may be formed in a cutting area. As shown in FIG. 1, a structure for optical measurement 1 includes a plurality of repeating units along a direction A, e.g., a straight line. The structure for optical measurement 1 is made of the same material(s) as the corresponding semiconductor device and is formed through the same steps. The structure for optical measurement 1 has identical structural parameters as the corresponding semiconductor device. Therefore, structural parameters of the structure for optical measurement 1 may be used to represent structural parameters of the corresponding semiconductor structure. By measuring structural parameters of the structure for optical measurement, the structural parameters of the corresponding semiconductor device may be obtained.

Specifically, the conventional method of optical measurements includes several steps. First of all, as shown in FIG. 1, light spot 2 may be used to illuminate the structure for optical measurement 1 such that light scatters in the structure for optical measurement 1. Optical detectors receive the incident light and scattered light for analysis and modulation. A measured scattering spectrum may be obtained.

Further, the obtained measured light scattering spectrum may be matched with each standard optical scattering spectrum in a library or database. If a match is obtained between the obtained light scattering spectrum and a standard optical scattering spectrum, the structural parameters of the standard semiconductor device structure corresponding to the standard optical scattering spectrum is considered as the structural parameters of the structure for optical measurement 1. The parameters of the standard semiconductor device structure corresponding to the standard optical scattering spectrum is further used as the structural parameters of the semiconductor device structure corresponding to the structure for optical measurement 1 and is used to estimate the quality of the semiconductor device structure. If no matching standard optical scattering spectrum may be found for the obtained light scattering spectrum, the structural parameters of the semiconductor device structure formed are considered as failing to meet the predetermined standards, and the semiconductor device structures are not qualified as good products.

Figure 2:
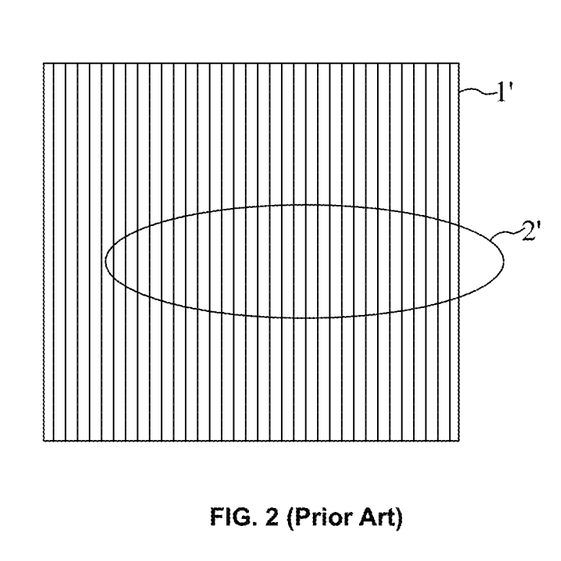
FIG. 2 illustrates the conventional measurement technique with light spot deviation.

However, in the conventional technology, as shown in FIG. 2, the light spot 2' often deviates from the area of the structure for optical measurement 1' and illuminates on a plain or void area on the substrate. Light reflection from the plain area may generate noise and reduce the reliability of the obtained light scattering spectrum. That is, the measured structure, reflected by the structural parameters, based on the obtained light scattering spectrum may not be accurate, and the obtained structural parameters of the semiconductor device structure may not be accurate.

Several solutions were developed to solve the problem mentioned above. For example, one solution includes increasing or expanding the size of the cutting area containing the structure for optical measurement. However, due to limited scribe-line space, such solution may be difficult to implement. Another solution includes decreasing or shrinking the size of the illuminating light spot to lower the probability of the light spot deviating from the structure for optical measurement so that the signal-to-noise ratio may be decreased. However, such solution often requires modifications to the corresponding equipment and thus the manufacturing cost may increase.

The disclosed methods and systems are directed to solve one or more problems set forth above and other problems.

BRIEF SUMMARY OF THE DISCLOSURE

One aspect of the present disclosure includes a method for optical measurements. The method includes providing a substrate with a structure for optical measurement on the substrate; and illuminating a light spot on the structure for optical measurement to obtain a measured light scattering spectrum. The method also includes performing a first matching process to obtain a plurality of matching standard optical scattering spectra and a plurality of first matching degrees, each standard optical scattering spectrum corresponding to one first matching degree; obtaining a plurality of combined optical scattering spectra based on the plurality of matching standard optical scattering spectra; and performing a second matching process to obtain a plurality second matching degree, each corresponding to one combined optical scattering spectrum.

Another aspect of the present disclosure includes a system for optical measurements. The system includes a measuring unit and a control unit. The control unit is configured to send commands to the measuring unit for performing optical measurements and process data sent from the measuring unit. The measuring unit is configured to receive the commands sent from the control unit to perform the optical measurement and send measured data to the control unit. The control unit is further configured to perform a first matching process to obtain a plurality of matching standard optical scattering spectra and a plurality of first matching degrees, each standard optical scattering spectrum corresponding to one first matching degree; obtain a plurality of combined optical scattering spectra based on the plurality of matching standard optical scattering spectra; and perform a second matching process to obtain a plurality second matching degree, each corresponding to one combined optical scattering spectrum.

Other aspects or embodiments of the present disclosure may be understood by those skilled in the art in light of the description, the claims, and the plottings of the present disclosure.

BRIEF DESCRIPTION OF THE PLOTTINGS

The following plottings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying plottings. Hereinafter, embodiments consistent with the disclosure will be described with reference to plottings. Wherever possible, the same reference numbers will be used throughout the plottings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

Through analyzing the existing problems in the conventional technology, it has been found that when a small portion of the light spot deviates from the structure for optical measurement, a matching standard optical scattering spectrum may still be found in the data base because of the small portion or area of the deviated light spot. However, the deviated portion of the light spot becomes a noise to the measured light scattering spectrum, and the measured light scattering spectrum may not accurately reflect the structural parameters of the structure for optical measurement. Thus, the obtained structural parameters of the corresponding semiconductor device structure may not be accurate.

To solve the problem in the conventional technology, the present disclosure provides an improved method for optical measurement. By using the provided method for optical scatterometry measurement, the first matching result may be tested to ensure the structural parameters obtained are accurate.

Figure 3:
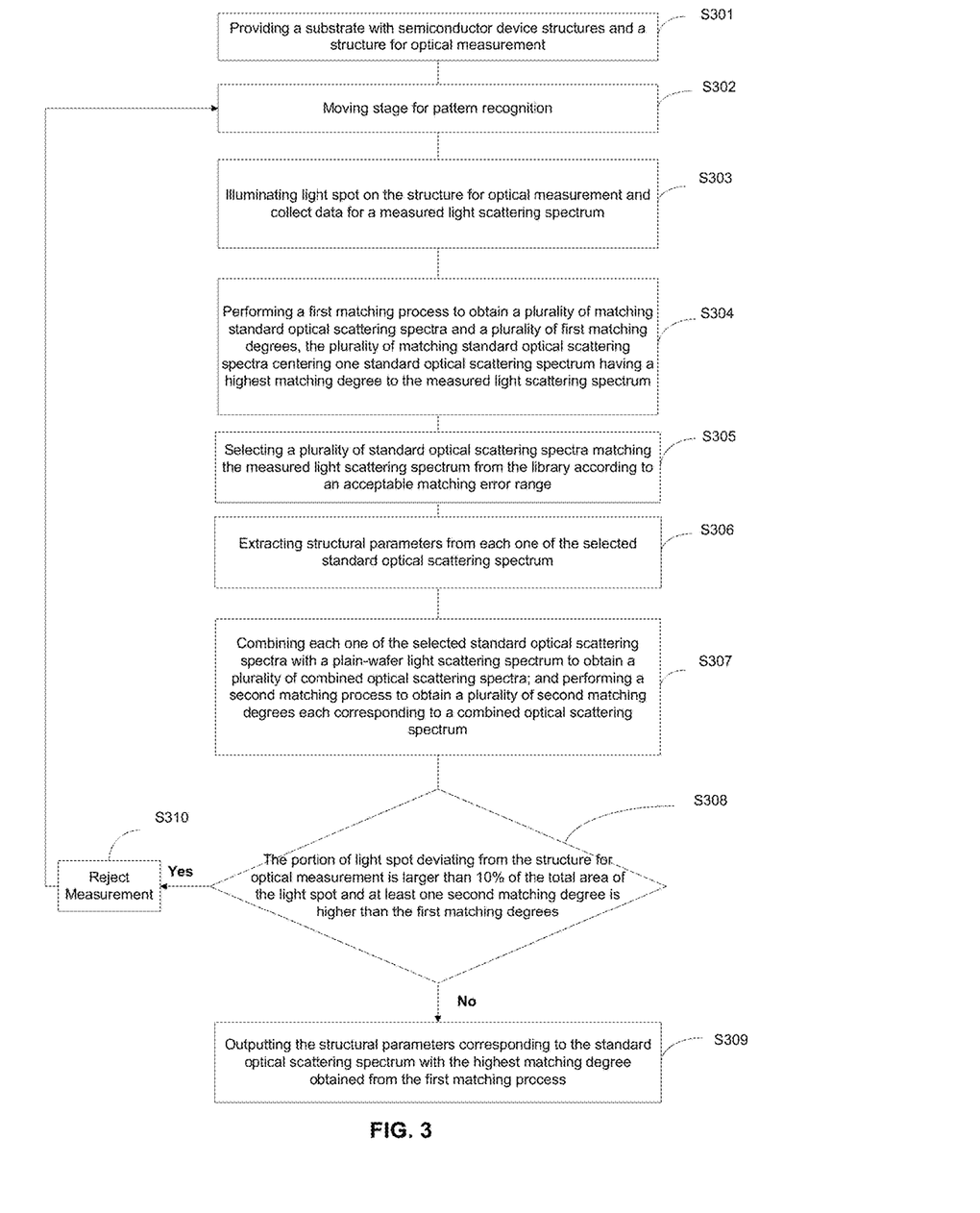
FIG. 3 illustrates the flow chart for an exemplary optical measurement process consistent with the disclosed embodiments.
Figure 4:
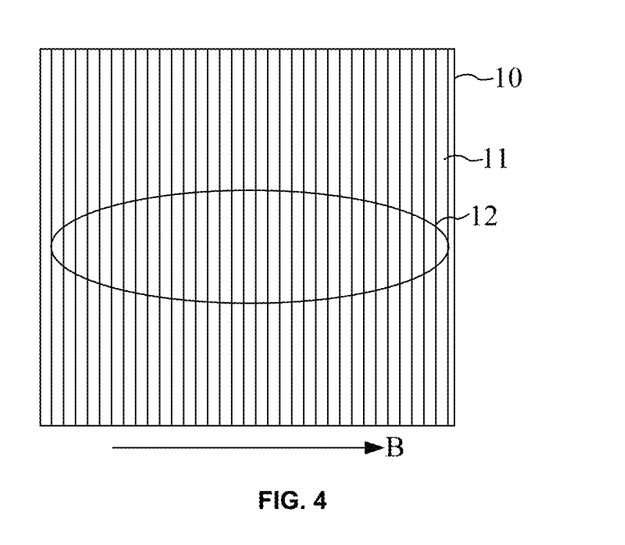
FIG. 4 illustrates the light spot illuminating on a structure for optical measurement for an exemplary optical measurement consistent with the disclosed embodiments.

As shown in FIGS. 3 and 4, at the beginning of the measurement, a substrate 10 may be provided (S301). The substrate 10 may include semiconductor device structures (not shown) and a structure for optical measurement 11 formed on the substrate 10. Semiconductor device structures and the structure for optical measurement 11 may be separated. The structure for optical measurement may be positioned in a cutting area and may only be used for the measurement for the semiconductor device structures. The structure for optical measurement 11 may not be a functional device and may be cut off or removed along a cutting line when the corresponding chip is subsequently diced.

In semiconductor manufacturing, the semiconductor device structures and structure for optical measurement 11 may be formed through same steps. For example, in the process of forming a MOS transistor, when the gate of the MOS transistor is being formed in the active region, a corresponding unit for optical measurement may be formed in the cutting area at the same time. That is, the unit for optical measurement and the gate of the MOS transistor may be formed simultaneously by the same deposition, photolithography, and etching processes. The structural parameters of the unit for optical measurement and the gate of the MOS transistor may be the same. For example, structure parameters such as gate length, gate width, gate height, and/or gate chamfer angle, may be identical. Same materials may be used to form the unit for optical measurement and the gate of the MOS transistor.

Thus, the structural parameters and impact (or variation) caused by the environment and/or equipment of the gate and the corresponding unit for optical measurement may be kept consistent. Structural parameters of the gate may be represented by the structural parameters of the corresponding unit for optical measurement. That is, by measuring the structural parameters of the unit for optical measurement, structural parameters of the corresponding gate may be obtained. The structural parameters may be used to determine whether the structural parameters of the gate meets predetermined designs or requirements. In semiconductor manufacturing, units or structures for optical measurement may be used to monitor and test structural parameters of the corresponding semiconductor device structures.

As shown in FIG. 4, the structure for optical measurement 11 may include a plurality of repeating units arranged along a direction B, e.g., a straight line, to form an array-like structure. When the semiconductor device structure is a single-layered structure along a direction perpendicular to the surface of the substrate 10, the structure for optical measurement 11 may also be a single-layered structure along a direction perpendicular to the surface of the substrate 10. When the semiconductor device structure is a multiple-layered structure along a direction perpendicular to the surface of the substrate 10, the structure for optical measurement 11 may also be a multiple-layered structure along a direction perpendicular to the surface of the substrate 10.

Returning to FIG. 3, after the substrate is provided, the stage holding the substrate may be moved for pattern recognition (S302).

The stage holding the substrate may be moved such that an automatic system may automatically perform pattern recognition on the substrate. The automatic system may move the stage to a proper position so that the light spot may be subsequently illuminated on the structure for optical measurement.

Returning to FIGS. 3 to 5, a light spot 12 may be used to illuminate the structure for optical measurement 11 and light scattering data may be collected automatically and a measured light scattering spectrum 13 may be formed automatically (S303). The measured light scattering spectrum 13 may be illustrated in $\lambda$-Rp coordinates, where $\lambda$ represents the wavelength of the scattering light, and Rp represents the intensity of the scattering light.

In one embodiment, as shown in FIG. 4, a lamp may be turned on to provide the light spot 12. The light spot 12 may have, but not limited to, an oval shape. The light spot 12 may also have a circular shape. The light spot 12 may be white light. The light beam may be incident on the structure for optical measurement 11 and may scatter. The intensity of light of one wavelength may attenuate differently compared with the intensity of light of another wavelength when transmitting through the repeating unit for optical measurements along the B direction. By collecting the scattered light using detectors and analyzing the collected result, a measured light scattering spectrum 13 can be obtained. The light intensity Rp as a function of wavelength $\lambda$ may be drawn and reflected in the measured light scattering spectrum 13. Thus, structural parameters of the structure for optical measurement 11 may be reflected in the measured light scattering spectrum 13.

Figure 7:
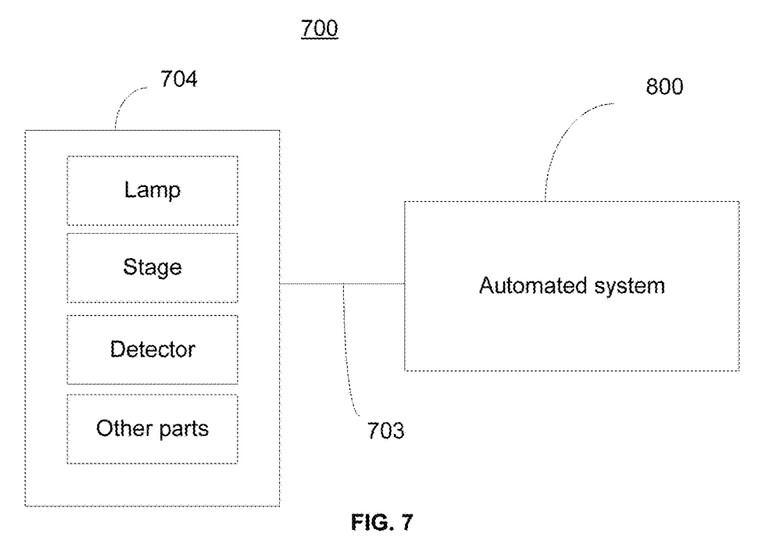
FIG. 7 illustrates an exemplary measuring equipment consistent with the disclosed embodiments.
Figure 8:
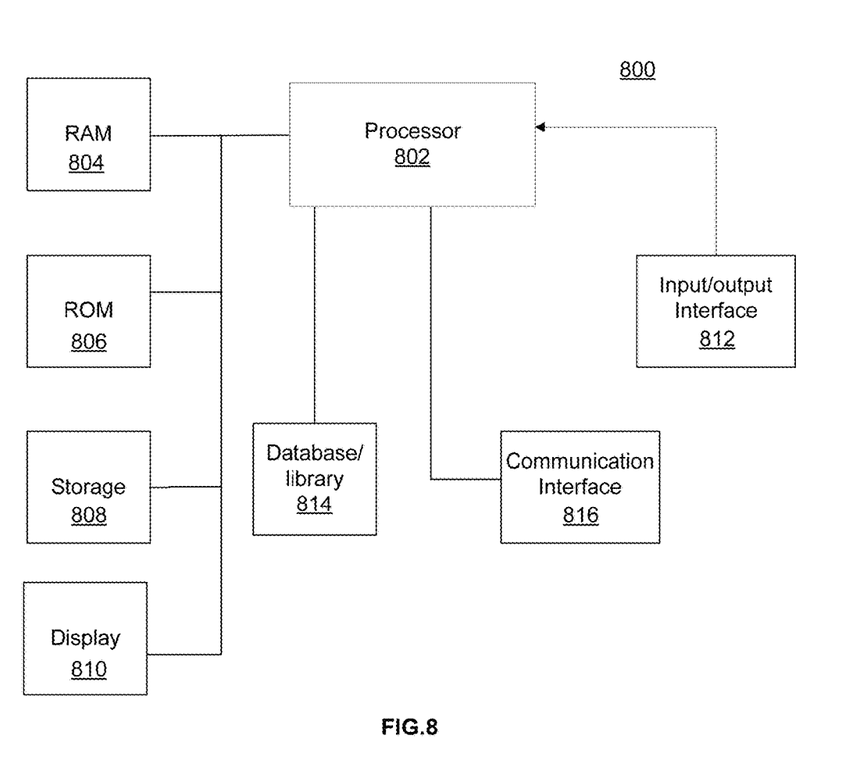
FIG. 8 illustrates a block diagram of an exemplary automated system consistent with the disclosed embodiments.

The automated system to control the collection of the scattered light and the plotting of the measured light scattering spectrum 13 may be shown in FIGS. 7 and 8. FIG. 7 illustrates an exemplary layout of a measuring equipment 700. In operation, an operator or a user may use one or more of measuring equipment 700 to measure the light scattering spectrum 13. The measuring equipment 700 can be programmed to execute certain commands and implement certain functions. For example, the operator may input commands to control the movement of the stage for pattern recognition, to collect light scattering data for plotting, and to process data for comparison and/or matching. The operator may click on suitable buttons on the measuring equipment to select the function(s) to be implemented or run all the functions automatically. The measuring equipment 700 may be any suitable measuring equipment having functions such as stage movement, data collection, and data processing.

FIG. 7 illustrates an exemplary measuring equipment 700. The measuring equipment 700 may include a measuring unit 704 and the automated system 800 connected to the measuring unit 704. The measuring unit 704 may include a lamp, a stage, at least one detector, a communication port (not shown), and other related parts. The lamp may be used to provide the light spot. The stage may be used to hold the substrate. The detector may be used to detect scattering light. The measuring unit 704 may be any suitable equipment capable of measuring the intensity of scattering light and send the light scattering data to the automated system 800. The communication port may be connected with the connection means 703. The connection means 703 may facility communication between the measuring unit 704 and the automated system 800. The connection means 703 may be any suitable connection for transferring commands from the automated system to the measuring unit 704 and transferring light scattering data from the measuring unit 704 to the automated system 800. For example, the measuring unit 704 may be a microscope with communication ports, the automated system may be a computer, and the connection 703 may be data lines and/or wireless connections.

The automated system 800, as shown in FIG. 8, may be a control unit for controlling the data collection and data processing of the measuring equipment 700. The automated system 800 may include a processor 802, a random access memory (RAM) unit 804, a read-only memory (ROM) unit 806, a storage unit 808, a display 810, an input/output interface unit 812, a library or database 814; and a communication interface 816. Other components may be added and certain devices may be removed without departing from the principles of the disclosed embodiments.

Processor 802 may include any appropriate type of general purpose microprocessor, digital signal processor or microcontroller, and application specific integrated circuit (ASIC). Processor 802 may execute sequences of computer program instructions or commands to perform various processes associated with the automated system 800. Computer program instructions may be loaded into RAM 804 for execution by processor 802 from read-only memory 806, or from storage 808. Storage 808 may include any appropriate type of mass storage provided to store any type of information that processor 802 may need to perform the processes. For example, storage 808 may include one or more hard disk devices, optical disk devices, flash disks, or other storage devices to provide storage space.

Display 810 may provide information to the operator of system 800. Display 810 may include any appropriate type of computer display device or electronic device display (e.g., CRT or LCD based devices). Input/output interface 812 may be provided for the operator to input information into automated system 800 or for the operator to receive information from system 800. For example, input/output interface 812 may include any appropriate input device, such as a keyboard, a mouse, an electronic tablet, voice communication devices, or any other optical or wireless input devices. Further, input/output interface 812 may receive from and/or send to other external devices.

Further, database/library 814 may include any type of commercial or customized database, and may also include analysis tools for analyzing the information in the databases. Database/library 814 may be used for storing information for semiconductor manufacturing and other related information. Communication interface 816 may provide communication connections such that automated system 800 may be accessed remotely and/or communicate with other systems such as the measuring unit 704 through computer networks or other communication networks via various communication protocols, such as transmission control protocol/internet protocol (TCP/IP), hyper text transfer protocol (HTTP), etc. The communication interface 816 may be connected to the connection means 703 and further connected to the measuring unit 704. Data may be transferred between the automated system 800 and measuring unit 704.

In one embodiment, an operator may input commands into the measuring equipment 700 by inputting command into the input/output interface 812. The processor 802 may accept and process the commands and send the related programs to the measuring unit 704 through the communication interface 816, the connection means 703, and the communication port of the measuring unit to start moving the stage for pattern recognition and subsequent automated processes such as light scattering data collection. The measuring unit 704 may execute the programs to collect light scattering data and send the collected light scattering data back to the automated system 800 for comparison or matching, and further functions. The communication interface 816 can communicate with certain parts of the measuring unit 700 shown in FIG. 7, such as the stage for holding the substrate and the detector to collect the scattering light, to execute the commands. Suitable data may be stored in ROM 806 and storage 808 to be processed. After the data is processed, result of a matching process, e.g., the first matching process, can be obtained. The result can be returned to the operator via the display 810 or the input/output interface 812. The result may also be stored in the ROM 806 and/or storage 808 for subsequent operations such as another matching process, e.g., the second matching process.

Figure 5:
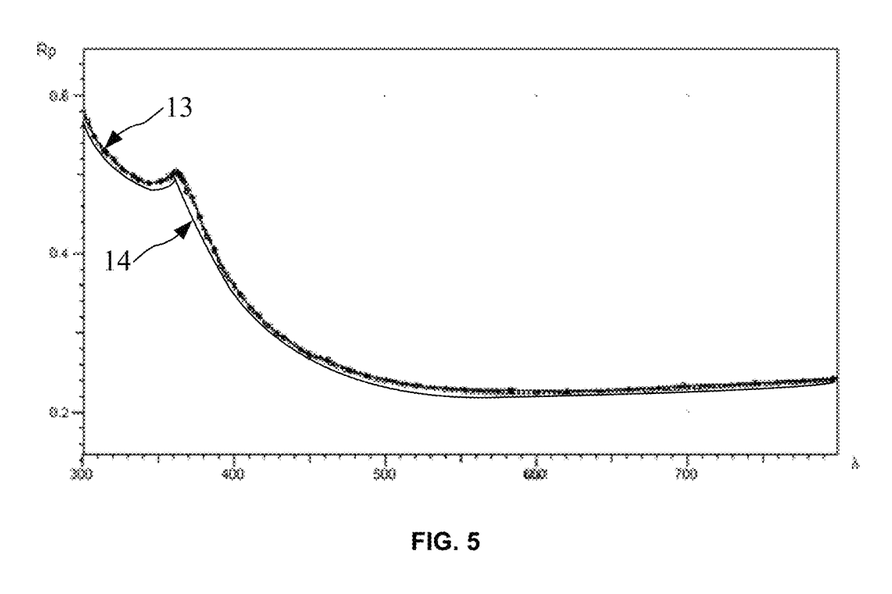
FIG. 5 illustrates a match between a measured light scattering spectrum and a standard optical scattering spectrum consistent with the disclosed embodiments.

Further, returning to FIG. 3 and FIG. 5, the obtained measured light scattering spectrum 13 may be compared to a plurality of standard optical scattering spectra 14 in the library for the first time, which can be referred as the first matching process (S304). A plurality of matching standard optical scattering spectra 14 may be obtained. A plurality of first matching degrees, each corresponding to the one of the plurality of the matching standard scattering spectra 14, may be obtained (8305). A matching degree may refer to the matching error between two comparing optical scattering spectra. For illustrative purposes. FIG. 5 may not show all the matching standard optical scattering spectra 14 and may only show one standard optical scattering spectrum for viewing simplicity.

It should be noted that, after measured light scattering spectrum 13 is compared to a plurality of standard optical scattering spectra 14 in the library for the first time, if no standard optical scattering spectrum 14 can be found to match the measured light scattering spectrum 13, the structural parameters of the semiconductor device structures corresponding to the structure for optical measurement may be regarded as not being able to meet the predetermined designs or requirements. The semiconductor device structures may be regarded as failing to meet manufacturing requirements and are thus discarded.

The library may be a collection of standard optical scattering spectra plotted based on predetermined structural parameters of the semiconductor device structures. That is, each standard optical scattering spectrum may correspond to a set of predetermined structural parameters. The standard optical scattering spectra do not include the scenario of light spot deviation so the standard optical scattering spectra may accurately reflect the structural parameters of the semiconductor device structure.

For example, a predetermined gate length may range from about c to about d, a predetermined gate width may range from about e to about f, and a predetermined gate height may range from about g to about h. Each value within the range of the predetermined gate length may be combined with each value within the range of the predetermined gate width and each value within the range of the predetermined gate height to plot a standard optical scattering spectrum. Thus, a plurality of values within the range of the predetermined gate width may be combined with a plurality of values within the range of the predetermined gate width and a plurality of values within the range of the predetermined gate height to plot a plurality of standard optical scattering spectra.

The measured light scattering spectrum 13 may be compared to each one of the standard optical scattering spectra 14 in the library. A match between the measured light scattering spectrum 13 and a standard optical scattering spectrum 14 may refer to, in the same A-Rp coordinates, the matching error between the measured light scattering spectrum 13 and the standard optical scattering spectrum 14 is within a certain acceptable range such that the measured light scattering spectrum 13 and the standard optical scattering spectrum 14 may substantially overlap. As described previously, in semiconductor manufacturing, fluctuation of structural parameters may be allowed within a certain range. A plurality of values selected for one structural parameter may be plotted to correspond to a plurality of standard optical scattering spectra 14. Thus, after the first matching, the measured light scattering spectrum 13 may match a plurality of standard optical scattering spectra 14 within the certain acceptable range.

In one embodiment, the selection of a plurality of standard optical scattering spectra 14 matching the measured light scattering spectrum 13 may include several steps. First, a standard optical scattering spectrum 14 having the highest first matching degree may be determined after the first matching process. The standard optical scattering spectrum 14 may have the lowest matching error compared to the measured light scattering spectrum 13. Further, a first set of structural parameters, corresponding to the standard optical scattering spectrum 14 with the highest first matching degree, may be determined. According to the number of types of the first set of structural parameters, a suitable range may be determined for each type of structural parameter based on the first set of structural parameters of the standard optical scattering spectrum 14 with the highest first matching degree. The first set of structural parameters may be gate structural parameters such as the gate length, gate width, and gate height. Further, a plurality of standard optical scattering spectra 14, each including structural parameters within the suitable ranges, may be determined (S306).

For example, for the gate of a MOS transistor, the standard optical scattering spectrum 14 having the highest first matching degree to the measured light scattering spectrum 13 may correspond to a gate length of 10 (the number 10 is only used to exemplify the embodiment and does not represent the true value of the gate length). A suitable range of the gate length may be 10, 10±1, 10±2, and 10±3. A suitable range of the gate width and a suitable range of the gate height may be determined similarly. The suitable range of each type of structural parameter may ensure a number of about 10 to 1000 standard optical scattering spectra 14 to be eventually selected. In one embodiment, about 10 to 100 standard optical scattering spectra 14 may be selected. If the number of standard optical scattering spectra 14 is overly small after the first matching process, the result of the optical measurement may be regarded not accurate. If the number of standard optical scattering spectra 14 is overly large after the first matching process, the time for the optical measurement may be too long.

Figure 6:
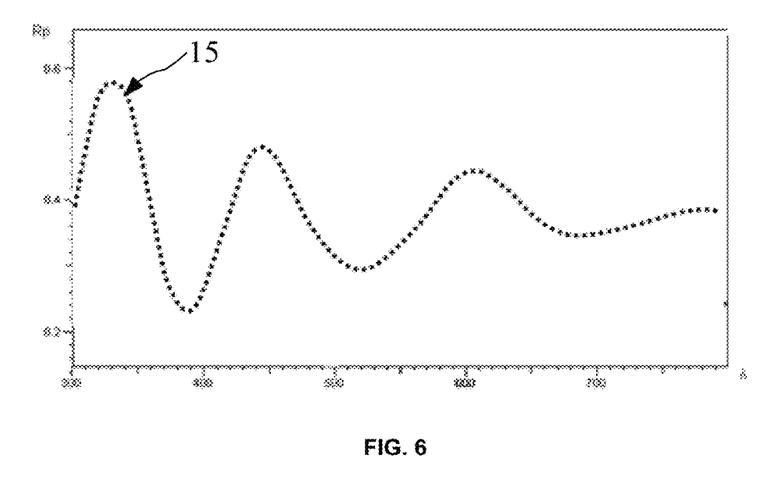
FIG. 6 illustrates an exemplary light scattering spectrum formed by light spot illuminating on a plain area of the substrate consistent with the disclosed embodiments.

Further, returning to FIG. 3 and FIG. 6, a plain-wafer light scattering spectrum 15 may be provided. The plain-wafer light scattering spectrum 15 may be obtained by illuminating the light spot 2 on a plain wafer. Each of the standard optical scattering spectrum 14 obtained in the first matching process may be combined, superimposed, or attached with the plain-wafer light scattering spectrum 15 according to a ratio of (a %:b %), where a %+b %=100% and 0<a,b<100. A plurality of superimposed optical scattering spectra may be obtained corresponding to each standard optical scattering spectrum 14 (S307). In one embodiment, b % may be greater than zero and less than or equal to 10%. Accordingly, a % may be greater than or equal to 90% and less than 100%.

A small portion of the light spot may deviate from the structure for optical measurement and may cause the result of the optical measurement to be inaccurate, where the small portion may refer to an area less than 10% of the total area of the light spot. Having a light spot with larger than 10% of the total area of the light spot deviating from the structure for optical measurement may be very rare and may thus be ignored in practice. Even if larger than 10% of the total light spot deviates from the structure for optical measurement, it may also be impossible to find any matching standard optical scattering spectra after the first matching process. Thus, when superimposing the plain-wafer light scattering spectrum 15 with the plurality of standard optical scattering spectra 14, b % should not exceed 10%. Also, because there may be a sufficient number of selected standard optical scattering spectra 14 after the first matching, the value of b % should be chosen reasonably within the range of b %. Thus, the number of the superimposed optical scattering spectra is not overly large. The time for a second matching process and the time required for the overall optical measurement may be shortened.

Further, a second matching may be performed (S308). The measured spectrum 13 may be compared with each one of the superimposed optical scattering spectrum to obtain a plurality of second matching degree. Each one of the plurality of second matching degree may be correspond to one superimposed optical scattering spectrum. After the second matching process, if each one of the second matching degree is less than all of the first matching degrees, it can be considered that the light spot did not deviate from the structure for optical measurement when light spot illuminated on the structure for optical measurement. The measured light scattering spectrum 13 may truly and accurately reflect the structural parameters of the corresponding semiconductor device structures.

Further, the standard structural parameters corresponding to the standard optical scattering spectrum 14, obtained through the first matching process and having the highest first matching degree to the measured light scattering spectrum 13, may be selected as output (S309). The outputted structural parameters may thus be the structural parameters of the corresponding semiconductor device structures. The outputted structural parameters may be shown on the display of the measuring equipment.

If at least one second matching degree is higher than the first matching degrees, it may be considered that the light spot deviated from the structure for optical measurement when light spot illuminated on the structure for optical measurement. It may be necessary to reject the measured light scattering spectrum 13 return to the second step illustrated in FIG. 3, i.e., moving the stage for pattern recognition, and repeat the measurement process in FIG. 3 (S310).

By using the method of optical measurement disclosed in one embodiment, when the light spot is illuminating on the structure for optical measurement, several scenarios may occur.

The light spot may not deviate from the structure for optical measurement. If the structural parameters corresponding to the structure for optical measurement are within the predetermined range, standard optical scattering spectra having desirably high matching degrees may be selected from the library through the first matching process. In this case, if a plain-wafer light scattering spectrum is introduced and superimposed with each one of the matching standard optical scattering spectrum, the superimposed optical scattering spectra may each have a large error when compared with the measured light scattering spectrum.

The light spot may deviate from the structure for optical measurement. If a large portion of the light spot deviates from the structure for optical measurement, no matching standard optical scattering spectrum may be found or selected after the first matching process, and the corresponding semiconductor device structure may be considered as inferior. No subsequent second matching process is needed. If a small portion of the light spot deviates from the structure for optical measurement, the measured light scattering spectrum may thus be a superimposition or combination of the light scattering spectrum formed by the portion of light spot illuminating on the structure for optical measurement and the plain-wafer light scattering spectrum. Because the portion of the light spot deviating from the structure for optical measurement may be sufficiently small, the plain-wafer light scattering spectrum may not be considered as a high noise to the measured light scattering spectrum. Thus, after the first matching, standard optical scattering spectra, each with a sufficiently high matching degree, may still be obtained. However, the obtained standard optical scattering spectra may not truly and accurately reflect the structural parameters of the structure for optical measurement. As a result, the comparability between the measured light scattering spectrum and a standard optical scattering spectrum may decrease because of the noise.

Thus, if the noise, caused by the plain-wafer light scattering spectrum, is introduced into the standard optical scattering spectra, an improved comparability and smaller error between the measured light scattering spectrum and a superimposed optical scattering spectrum may be obtained. Considering the library has a large number of standard optical scattering spectra, it may be impossible or difficult to introduce the noise into every standard optical scattering spectrum. Thus, in one embodiment, after the first matching process, a plurality of standard optical scattering spectra substantially matching the measured light scattering spectrum may be selected and the plain-wafer light scattering spectrum may be introduced into each one of the selected standard optical scattering spectrum.

Because the portion of light spot deviating from the structure for optical measurement may have a sufficiently small area, the measured light scattering spectrum with the noise may have a sufficiently small error compared with the measured light scattering spectrum without the noise. It may be considered that, in the first matching process, the standard optical scattering spectrum with the highest first matching degree, obtained based on the measured light scattering spectrum with the noise, and a plurality of standard optical scattering spectra centering the standard optical scattering spectrum with the highest first matching degree, may include one standard optical light scattering spectrum that can truly reflect the structural parameters of the measured light scattering spectrum. If the noise is introduced into the one standard optical scattering spectrum, an error between the one standard optical scattering spectrum and the measured light scattering spectrum may be even lower. It may thus be accurately concluded that the light spot deviated from the structure for optical measurement.

Thus, by providing a second matching process based on the first matching process, the second matching process may be used to test the accuracy of the result obtained from the first matching process. Accuracy of the final result of the optical measurement may be ensured. Thus, the disclosed method may effectively improve the accuracy of the optical measurement and further improve the accuracy of the measured structural parameters of the semiconductor device structures. Quality of the semiconductor device structures may be accurately estimated. Also, the number of the superimposed optical scattering spectra in the second matching process is far less than the number of matching standard optical scattering spectra in the first matching process. Thus, the second matching process may only take a desirably short time.

In addition, if, after the second matching process, at least one second matching degree is higher than the first matching degrees, a statistical analysis may be performed to analyze the result of the second matching process. Specifically, the statistical analysis may be a hypothesis test. A hypothesis test may refer to assuming when the light spot illuminates on the structure for optical measurement, the light spot does not deviate from the structure for optical measurement, which means the result of the first matching process is accurate and the probability of the measured light scattering spectrum 13 matching a superimposed optical scattering spectra after the second matching process is sufficiently small. The small probability event may be significantly less likely to happen.

A predetermined probability of the measured light scattering spectrum 13 matching a superimposed optical scattering spectrum may be defined. The predetermined probability may range from about 0.01 to about 0.05. For example, the predetermined probability may be 0.05, 0.03, or 0.01. A smaller predetermined probability may represent a more accurate statistical result. If the second matching process shows the small probability event has happened, i.e., the probability of a second matching degree being higher than the first matching degrees is higher than or equal to the predetermined probability, the hypothesis may be considered completely wrong. The real event is the light spot deviates from the structure for optical measurement.

In certain applications, the selected standard optical scattering spectra from the first matching process may be regarded as an N dimensional best match or fit subset, which has a degree of freedom (DoF)) of N. A standard optical scattering spectrum may be regarded a model. The number of the selected standard optical scattering spectra may be about 10 to 1000. The plain-wafer light scattering spectrum may be a thin-film pad scatterometry model spectrum and may be regarded as a sub dimension. After the plain-wafer light scattering spectrum is attached with each one of the selected standard optical scattering spectrum, the N dimensional best match subset may become an (N+1) dimensional subset, which has a DoF of (N+1). A fast second matching process may be performed between the measured light scattering spectrum and each spectrum in the (N+1) dimensional subset.

Although the disclosed method may not have the best accuracy in certain embodiments, the disclosed method is sensitive to light spot deviation or shift and off-the-target spectral response. Thus, in some embodiments, the disclosed method may be used as a fast real time gauge to determine whether the light spot has deviated to an extent that the result of the measurement cannot be trusted.

Accordingly, in the disclosed method of optical measurement, after the first matching process, a plurality of matching standard optical scattering spectra may be selected. The plurality of matching standard optical scattering spectra each has an acceptable or reasonable error compared to the measured light scattering spectrum. First matching degrees may be obtained. Further, a plain-wafer light scattering spectrum is superimposed with each of the matching standard optical scattering spectra according to a certain ratio to obtain a plurality of superimposed optical scattering spectra.

Further, the measured light scattering spectrum is compared with each superimposed optical scattering spectrum for a second matching process to obtain a second matching degree for each superimposed optical scattering spectrum. If each of the second matching degree is lower than the first matching degrees, it may be considered that when the light spot illuminated on the structure for optical measurement, the light spot did not deviate from the structure for optical measurement.

The measured spectrum truly and accurately reflects structural parameters of the semiconductor device structure. Structural parameters of the standard optical scattering spectrum, obtained from the first matching process and having the highest first matching degree matching to the measured spectrum, is selected and outputted. The outputted structural parameters may be the structural parameters of the corresponding semiconductor device structure.

If at least one second matching degree is higher than the first matching degrees, it may be considered that the light spot deviated from the structure for optical measurement when the light spot illuminated on the structure for optical measurement. It may be necessary to repeat the measurement process from the beginning, e.g., for at least once, until each one of the second matching degrees is lower than the first matching degrees.

In the disclosed method, the second matching process may be used to test the accuracy of the first matching process to ensure the final result of the optical measurement is accurate. Thus, the accuracy of the optical measurement may be greatly improved, and the accuracy of the measured structural parameters of the semiconductor device structure may be further improved. The quality of the semiconductor device structures may be accurately estimated. In addition, the number of superimposed optical scattering spectra in the second matching process is far less than the number of matching standard optical scattering spectra in the first matching process. Thus, the second matching does not require an undesirably long time to complete and may only require a short period of time.

Thus, by using the disclosed method, scatterometry measurement with outside noise can be automatically detected and discarded. The precision, accuracy, and repeatability of the scatterometry measurement may be improved.

Other embodiments of the disclosure will be apparent to those skilled in the art from consideration of the specification and practice of the invention disclosed herein. It is intended that the specification and examples be considered as exemplary only, with a true scope and spirit of the invention being indicated by the claims.

What is claimed is:

1. A method for optical measurements, comprising:
   providing a substrate with a structure for optical measurement on the substrate;
   illuminating a light spot on the structure for optical measurement to obtain a measured light scattering spectrum;
   performing a first matching process to obtain a plurality of matching standard optical scattering spectra and a plurality of first matching degrees, each matching standard optical scattering spectrum corresponding to one first matching degree, wherein each first matching degree is a matching error between the measured light scattering spectrum and each matching standard optical scattering spectrum;
   obtaining a plurality of combined optical scattering spectra based on the plurality of matching standard optical scattering spectra; and
   performing a second matching process to obtain a plurality second matching degree, each corresponding to one combined optical scattering spectrum, wherein each second matching degree is a matching error between the measured light scattering spectrum and each combined optical scattering spectrum.

2. The method according to claim 1, further including:
   when no second matching degree is higher than the first matching degrees, selecting a matching standard optical scattering spectrum with a highest first matching degree from the plurality of matching standard optical scattering spectra and outputting structural parameters corresponding to the matching standard optical scattering spectrum with the highest first matching degree; and
   when at least one second matching degree is higher than any one of the first matching degrees, continuing the illuminating the light spot on the structure for optical measurement and performing the optical measurement until each one of the second matching degrees is lower than the first matching degrees.

3. The method according to claim 1, wherein the plurality of combined optical scattering spectra is formed by:
    illuminating the light spot on a plain wafer to obtain a plain-wafer light scattering spectrum; and
    attaching a first percentage (a %) of the plain-wafer light scattering spectrum with a second percentage (b %) of each one of the matching standard optical scattering spectra to obtain the plurality of combined optical scattering spectra, wherein the first percentage and the second percentage have the relationship that a %+b %=100% and 0<a,b<100, and values of a and b are varied to be combined with each one of the standard optical scattering spectra.

4. The method according to claim 3, wherein:
    in the first matching process, the measured light scattering spectrum is compared with a plurality of standard optical scattering spectra to obtain the matching standard optical scattering spectra; and
    each one of the matching standard optical scattering spectra is combined with the plain-wafer light scattering spectrum to obtain the plurality of combined optical scattering spectra.

5. The method according to claim 4, wherein a subset of the matching standard optical scattering spectra has a degree of freedom of N, and a subset of the combined optical scattering spectra has a degree of freedom of (N+1).

6. The method according to claim 4, wherein:
    after the first matching process, when the measured light scattering spectrum has no match with any one of the plurality of standard optical scattering spectra, a semiconductor device structure corresponding to the structure for optical measurement is determined as inferior.

7. The method according to claim 2, wherein obtaining the plurality of matching standard optical scattering spectra further includes:
    after the first matching process, obtaining the matching standard optical scattering spectrum with the highest first matching degree to the measured light scattering spectrum;
    obtaining a first set of structural parameters corresponding to the matching standard optical scattering spectrum with the highest first matching degree;
    according to predetermined value ranges for the standard structural parameters, determining a plural sets of standard structural parameters based on the first set of structural parameters, wherein the plural sets of standard structural parameters include the first set of structural parameters; and
    obtaining the plurality of matching standard optical scattering spectra each corresponding to one of the plural sets of structural parameters.

8. The method according to claim 2, wherein the second matching process further includes a statistical analysis, and the statistical analysis includes:
    assuming a probability of a second matching degree higher than the first matching degrees to be a predetermined probability value; and
    after comparing each second matching degree to the first matching degrees, when an event of at least one second matching degree being higher than the first matching degrees occurs, a probability of the event is higher than or equal to the predetermined probability value and the optical measurement returns to illuminating the light spot on the structure for optical measurement and performing the optical measurement for at least once until each one of the second matching degrees is lower than the first matching degrees.

9. The method according to claim 8, wherein the predetermined probability value ranges from about 0.01 to about 0.05.

10. The method according to claim 1, wherein a number of the matching standard optical scattering spectra ranges from about 10 to about 1000.

11. The method according to claim 10, wherein a number of the matching standard optical scattering spectra ranges from about 10 to about 100.

12. The method according to claim 3, wherein b % is less than 10%.

13. The method according to claim 1, wherein the structure for optical measurement includes a plurality of repeating units along a straight direction.

14. A system for optical measurements, comprising a measuring unit and a control unit, wherein:
    the control unit is configured to send commands to the measuring unit for performing optical measurements and process data sent from the measuring unit;
    the measuring unit is configured to receive the commands sent from the control unit to perform the optical measurement and send measured data to the control unit; and
    the control unit is further configured to:
    obtain a measured light scattering spectrum;
    perform a first matching process to obtain a plurality of matching standard optical scattering spectra and a plurality of first matching degrees, each matching standard optical scattering spectrum corresponding to one first matching degree, wherein each first matching degree is a matching error between the measured light scattering spectrum and each matching standard optical scattering spectrum;
    obtain a plurality of combined optical scattering spectra based on the plurality of matching standard optical scattering spectra; and
    perform a second matching process to obtain a plurality second matching degree, each corresponding to one combined optical scattering spectrum, wherein each second matching degree is a matching error between the measured light scattering spectrum and each combined optical scattering spectrum.

15. The system according to claim 14, wherein, to perform the first matching process, the measuring unit is further configured to:
    illuminating the light spot on a structure for optical measurement to collect light intensity data of scattering light and sending the collected light intensity data to the control unit;
    wherein the control unit is configured to generate the measured light scattering spectrum based on collected light intensity data, and to compare the measured light scattering spectrum with the plurality of standard optical scattering spectra to obtain a plurality of matching standard optical scattering spectra.

16. The system according to claim 14, wherein:
    the measuring unit is configured to illuminate the light spot on a plain wafer and sends collected light scattering data; and
    the control unit is configured to generate a plain-wafer light scattering spectrum; and to combine each one of the matching standard optical scattering spectra with the plain-wafer light scattering spectrum to obtain a plurality of combined optical scattering spectra.

17. The system according to claim 16, wherein the second matching process includes a statistical analysis, the statistical analysis including:
- the user or the control unit being configured to assume a probability of a second matching degree higher than the first matching degrees to be a predetermined probability value; and
- after comparing each second matching degree to the first matching degrees, when an event of at least one second matching degree being higher than the first matching degrees occurs, a probability of the event is higher than or equal to the predetermined probability value and the control unit is configured to return to illuminating the light spot on the structure for optical measurement and performing the optical measurement for at least once until each one of the second matching degrees is lower than the first matching degrees.

18. The system according to claim 16, wherein:
- when no second matching degree is higher than the first matching degrees, the control unit is configured to select a matching standard optical scattering spectrum with a highest first matching degree from the plurality of matching standard optical scattering spectra and outputting structural parameters corresponding to the matching standard optical scattering spectrum with the highest first matching degree; and
- when at least one second matching degree is higher than any one of the first matching degrees, the control unit is configured to continue illuminating the light spot on the structure for optical measurement and performing the optical measurement for at least once until each one of the second matching degrees is lower than the first matching degrees.

* * * * *